US009775667B2

(12) United States Patent
Korvick et al.

(10) Patent No.: US 9,775,667 B2
(45) Date of Patent: Oct. 3, 2017

(54) SURGICAL INSTRUMENT WITH ARTICULATION INDICATOR

(71) Applicant: Ethicon Endo-Surgery, Inc., Cincinnati, OH (US)

(72) Inventors: Donna L. Korvick, Maineville, OH (US); Barry C. Worrell, Centerville, OH (US)

(73) Assignee: Ethicon LLC, Guaynabo, PR (US)

( * ) Notice: Subject to any disclaimer, the term of this patent is extended or adjusted under 35 U.S.C. 154(b) by 405 days.

(21) Appl. No.: 13/920,207

(22) Filed: Jun. 18, 2013

(65) Prior Publication Data
US 2014/0371737 A1  Dec. 18, 2014

(51) Int. Cl.
| | | |
|---|---|---|
| A61B 18/12 | (2006.01) |
| A61B 18/14 | (2006.01) |
| A61B 1/008 | (2006.01) |
| A61B 18/00 | (2006.01) |
| A61B 90/00 | (2016.01) |

(52) U.S. Cl.
CPC .......... A61B 18/1445 (2013.01); *A61B 1/008* (2013.01); *A61B 2018/00202* (2013.01); *A61B 2018/1455* (2013.01); *A61B 2090/0811* (2016.02)

(58) Field of Classification Search
CPC ............ A61B 18/1442; A61B 18/1445; A61B 18/1447; A61B 2018/145; A61B 2018/1452; A61B 2018/14525; A61B 1/00149; A61B 1/008; A61B 17/068; A61B 17/0682; A61B 17/0684; A61B 17/0686; A61B 17/072; A61B 17/07207
See application file for complete search history.

(56) References Cited

U.S. PATENT DOCUMENTS

| | | |
|---|---|---|
| 4,805,823 A | 2/1989 | Rothfuss |
| 5,415,334 A | 5/1995 | Williamson, IV et al. |
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |

(Continued)

OTHER PUBLICATIONS

U.S. Appl. No. 61/410,603, filed Nov. 5, 2010.
U.S. Appl. No. 61/550,768, filed Oct. 24, 2011.

*Primary Examiner* — Jaymi Della
(74) *Attorney, Agent, or Firm* — Frost Brown Todd LLC

(57) ABSTRACT

An apparatus for operating on tissue has a body, an elongate shaft, and an end effector. The elongate shaft extends distally from the body. The elongate shaft has an articulation section that is operable to selectively deflect the end effector laterally relative to the elongate shaft. The articulation section presents a first indication section and a second indication section. The first and second indication section may be configured to visually indicate the direction and degree of articulation of the articulation section. The first and second indication section may alternatively be configured to indicate the angular orientation of the end effector about the longitudinal axis. The body may further comprise a knob that is operable to rotate the shaft about the longitudinal axis. The knob may include a third indication section and a fourth indication section that align with the first and the second indication sections of the articulation section, respectively.

15 Claims, 16 Drawing Sheets

(56) References Cited

U.S. PATENT DOCUMENTS

| | | |
|---|---|---|
| 5,814,055 A | 9/1998 | Knodel et al. |
| 6,500,176 B1 | 12/2002 | Truckai et al. |
| 6,783,524 B2 | 8/2004 | Anderson et al. |
| 6,978,921 B2 | 12/2005 | Shelton, IV et al. |
| 7,000,818 B2 | 2/2006 | Shelton, IV et al. |
| 7,112,201 B2 | 9/2006 | Truckai et al. |
| 7,125,409 B2 | 10/2006 | Truckai et al. |
| 7,143,923 B2 | 12/2006 | Shelton, IV et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,303,108 B2 | 12/2007 | Shelton, IV et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 8,408,439 B2 | 4/2013 | Huang et al. |
| 8,453,914 B2 | 6/2013 | Laurent et al. |
| 8,461,744 B2 | 6/2013 | Wiener et al. |
| 2005/0273084 A1* | 12/2005 | Hinman et al. .................. 606/1 |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2008/0208129 A1* | 8/2008 | Carter et al. ............. 604/164.05 |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2012/0078243 A1* | 3/2012 | Worrell et al. ................. 606/33 |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116379 A1 | 5/2012 | Yates et al. |
| 2013/0023868 A1* | 1/2013 | Worrell ............ A61B 17/07207 606/33 |
| 2013/0030428 A1 | 1/2013 | Worrell et al. |

\* cited by examiner

SURGICAL INSTRUMENT WITH ARTICULATION INDICATOR

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011 (now U.S. Pat. No. 8,939,974), the disclosure of which is incorporated by reference herein; U.S. Pub. No. 2012/0083783, entitled "Surgical Instrument with Jaw Member," published Apr. 5, 2012 (now U.S. Pat. No. 8,888,809), the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,237, issued on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No 9,545,253, issued on Jan. 17, 2017, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
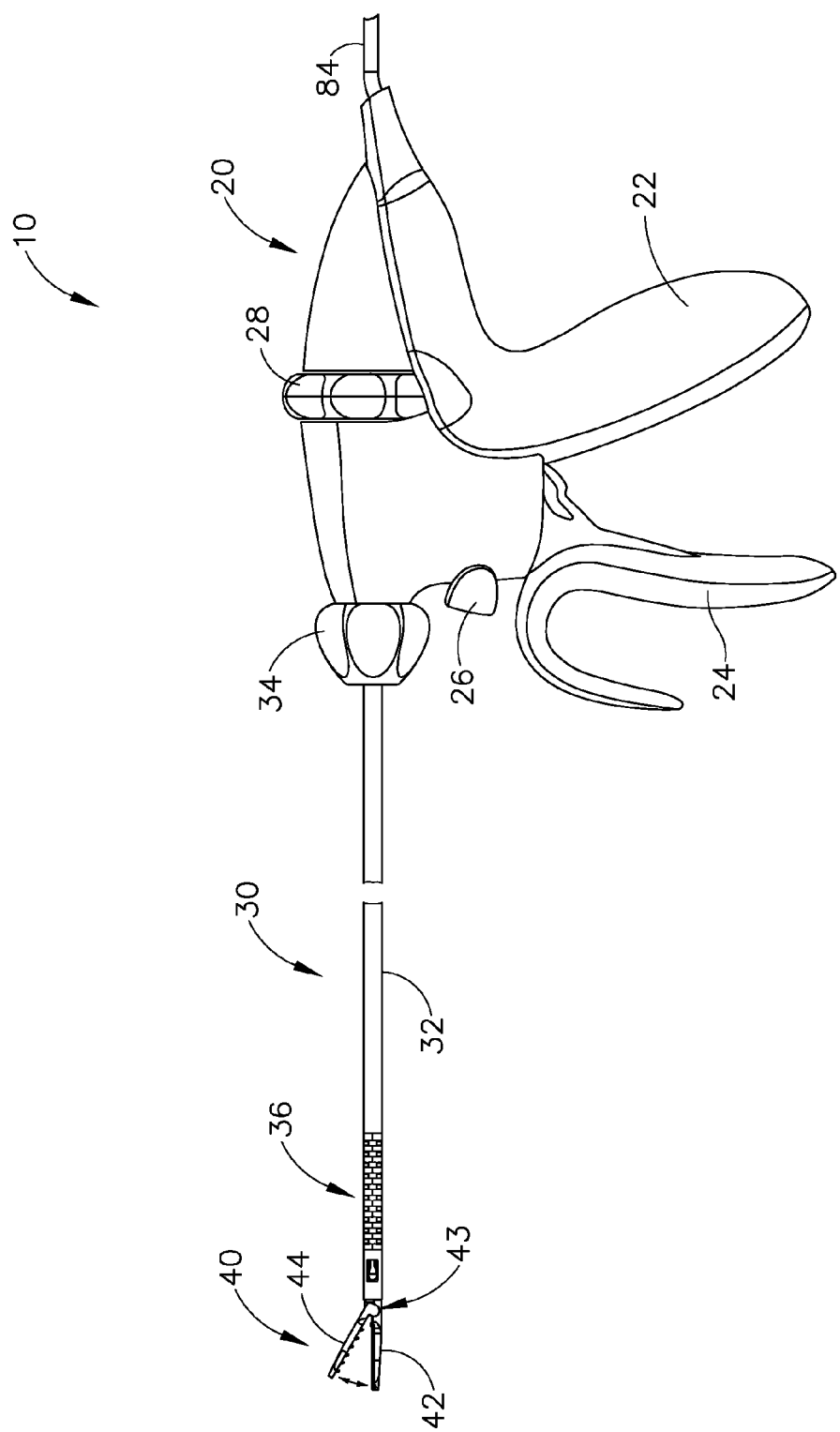
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218 (now U.S. Pat. No. 8,939,974); U.S. Pub. No. 2012/0083783 (now U.S. Pat. No. 8,888,809); U.S. Pub. No. 2012/0116379, now U.S. Pat. No. 9,161,803, issued Oct. 20, 2015; U.S. Pub. No. 2012/0078243; U.S. Pub. No. 2012/0078247; now U.S. Pat. No. 9,402,682, issued Aug. 2, 2016; U.S. Pub. No. 2013/0030428; now U.S. Pat. No. 9,089,327, issued on Jul. 28, 2015; and/or U.S. Pub. No. 2013/0023868, now U.S. Pat. No. 9,545,253, issued on Jan. 17, 2017. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued on Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, now U.S. Pat. No. 9,545,253, issued on Jan. 17, 2017, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
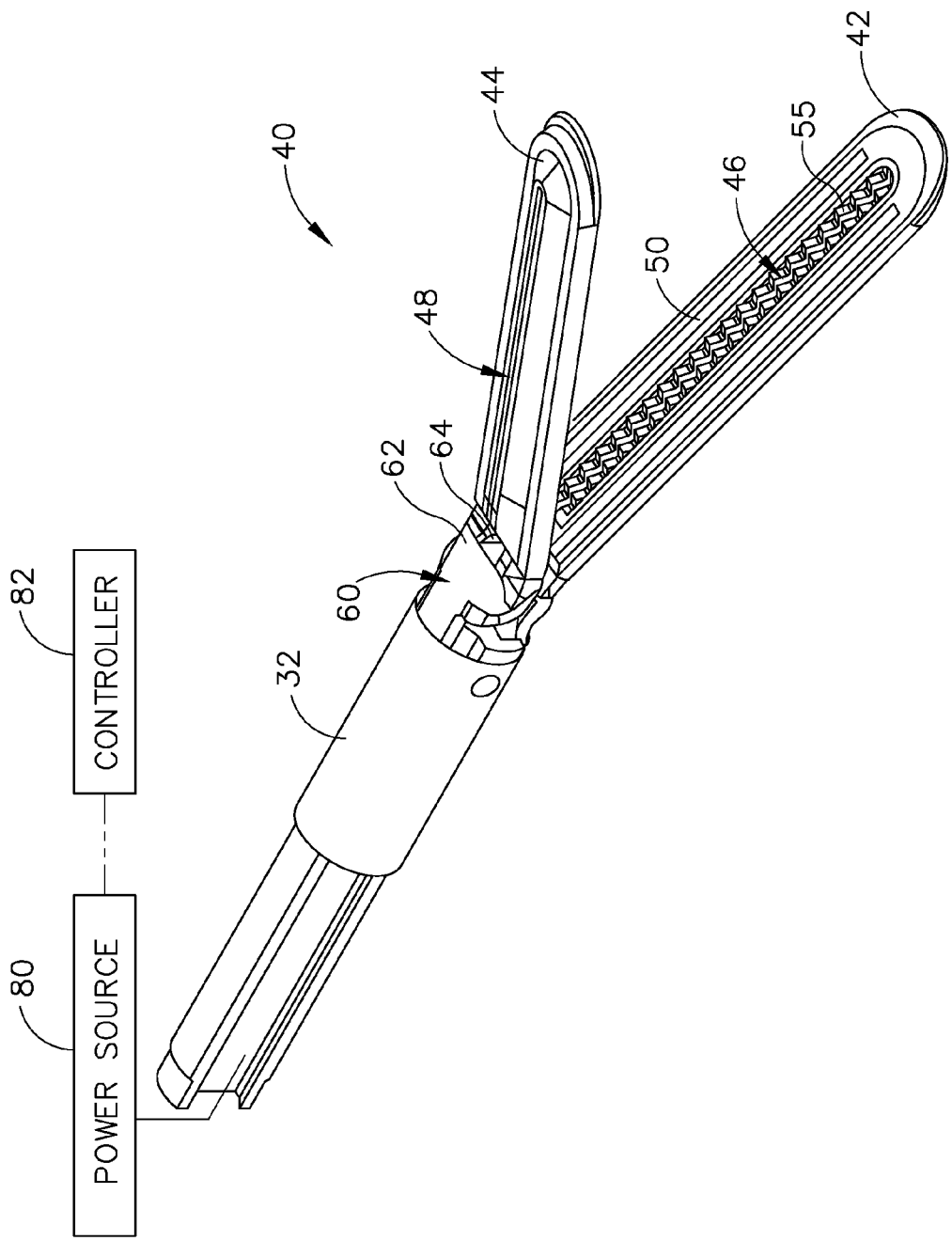
FIG. 2 depicts a perspective view of the end effector of the instrument of FIG. 1, in an open configuration.
Figure 3:
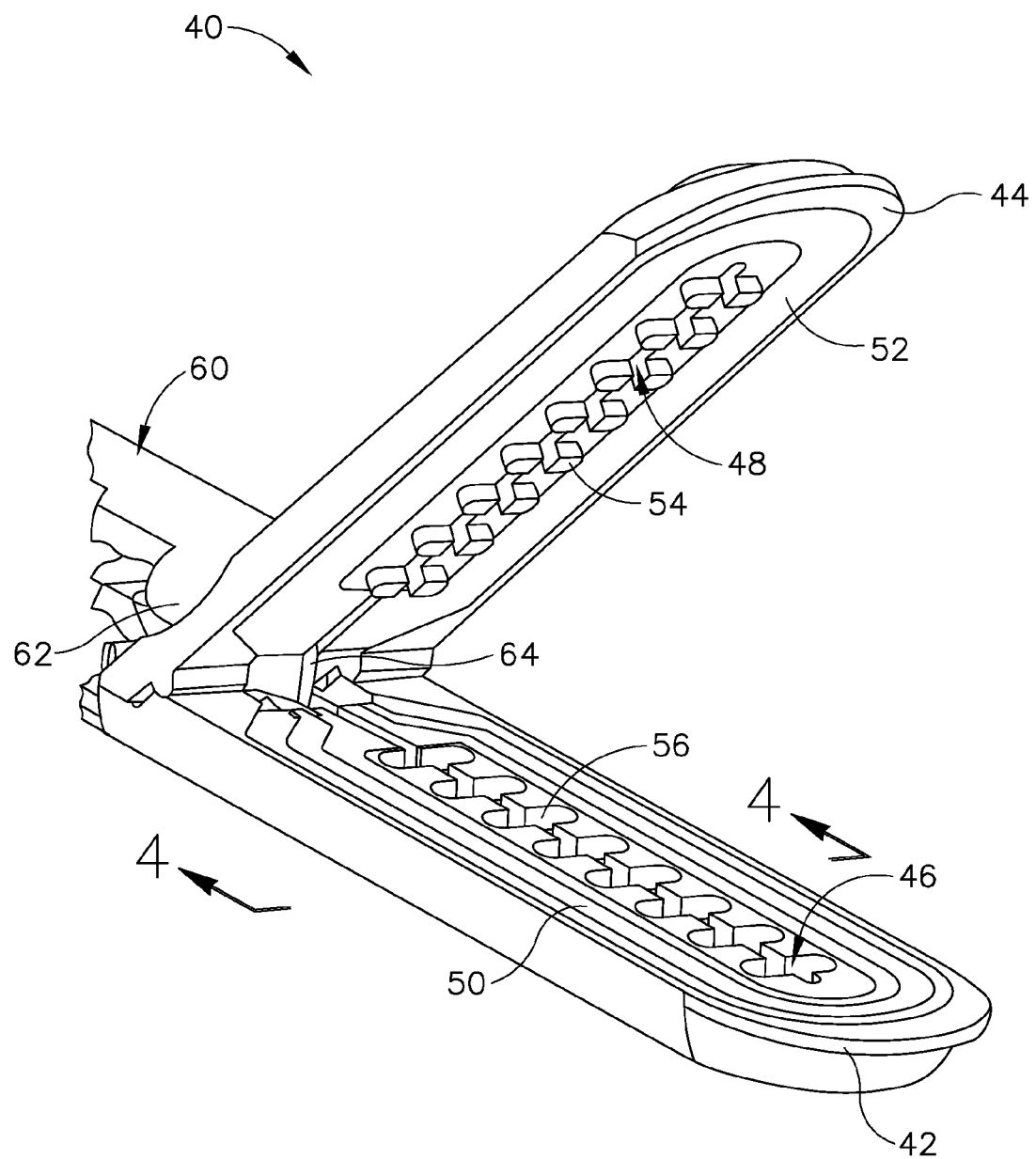
FIG. 3 depicts another perspective view of the end effector of the instrument of FIG. 1, in an open configuration.
Figure 4:
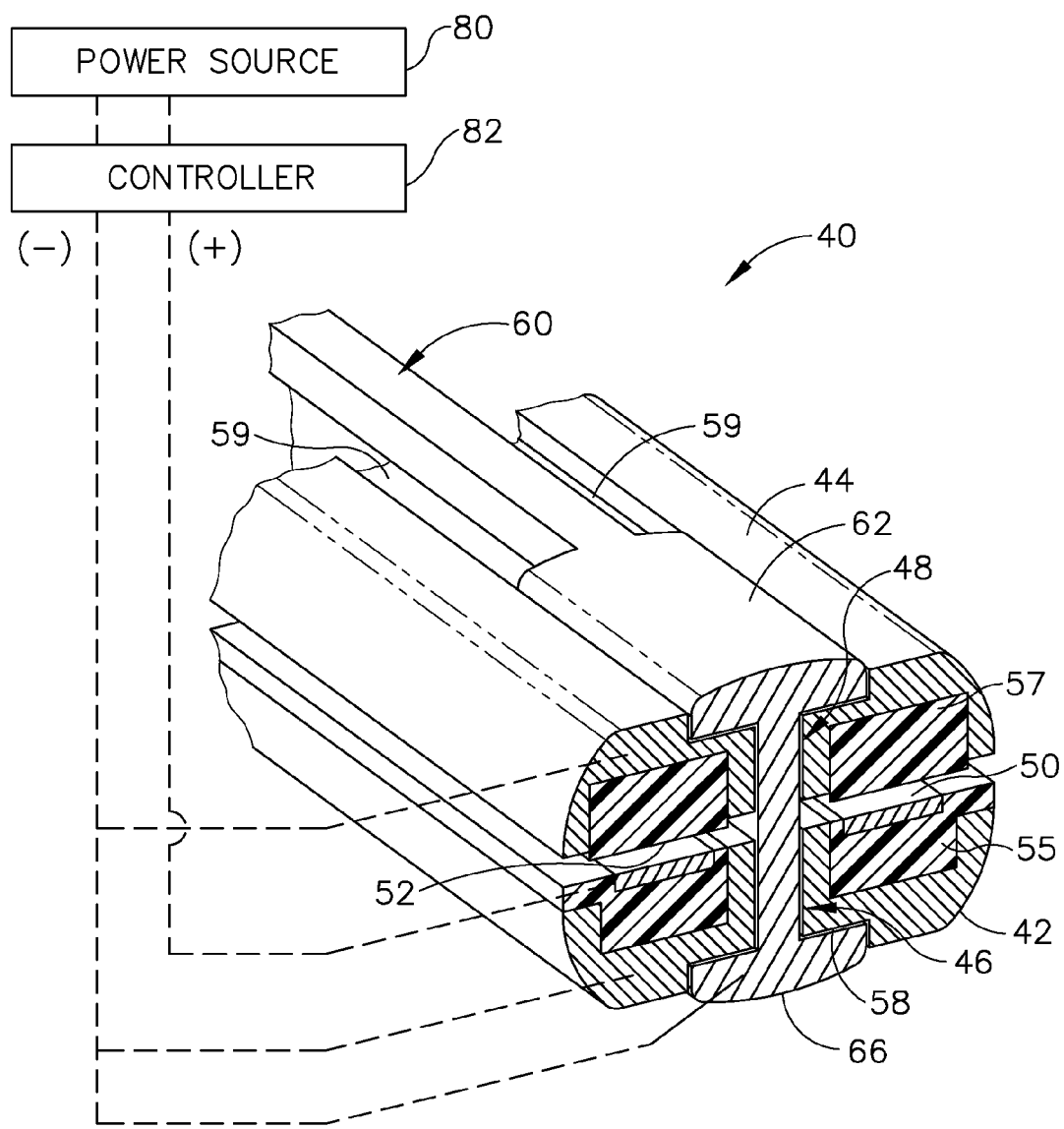
FIG. 4 depicts a cross-sectional end view, taken along line 4-4 of FIG. 3, of the end effector of FIG. 2, in a closed configuration and with the blade in a distal position

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at an active polarity while second electrode surface (52) serves as a reference/return passive electrode, such that RF current flows between electrode surfaces (50, 52) and thereby through tissue captured between jaws (42, 44). There are instances where the active signal crosses zero potential that the reference is at the same potential so there is no current flow. In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued on Jul. 28, 2015, the disclosure of which is incorporated by reference herein; U.S. Pub. No. 2011/0087212, entitled "Surgical Generator for Ultrasonic and Electrosurgical Devices," published Apr. 14, 2011 (now U.S. Pat. No. 8,986,302), the disclosure of which is incorporated by reference herein; U.S. Pub. No. 2011/0087213, entitled "Surgical Generator for Ultrasonic and Electrosurgical Devices," published Apr. 14, 2011 (now U.S. Pat. No. 8,951,248), the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued on May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011 (now U.S. Pat. No. 8,956,349), the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued on Jun. 23, 2015, the disclosure of which is incorporated by reference herein.

Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44). In some versions, serrations (46, 48) are electrically conductive.

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode.

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when an operator relaxes their grip on trigger (24).

Figure 5:
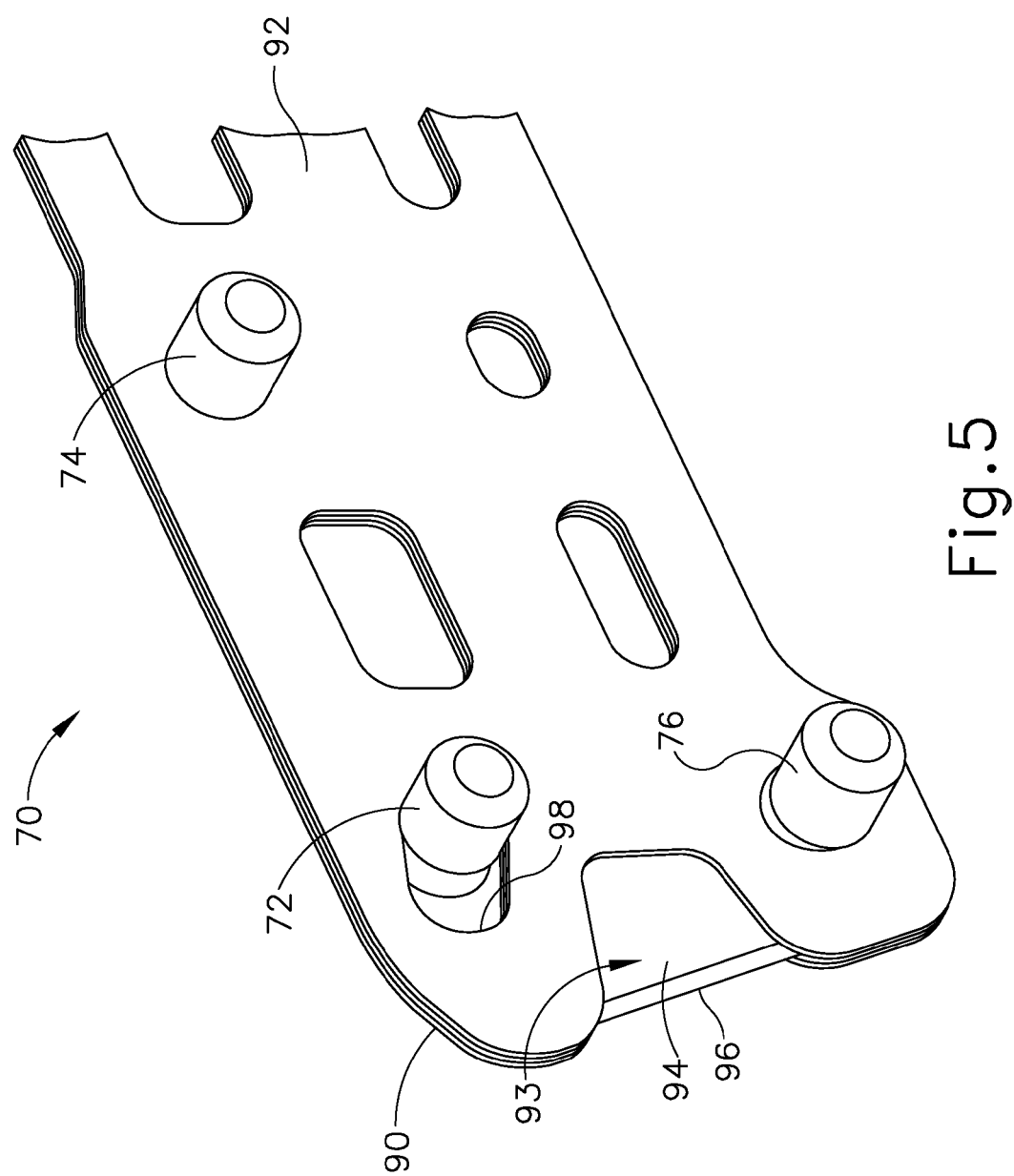
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Pins (72, 74, 76) may be pinged, upended, or otherwise configured to provide further retention in the body of firing beam (70). Of course, firing beam (70) may have any other suitable configuration. By way of example only, firing beam (70) may be configured in accordance with at least some of the teachings of U.S. Pub. No. 2012/0083783 (now U.S. Pat. No. 8,888,809), the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, help keep jaws (42, 44) in a closed and tightly clamping position. In particular, flanges (62, 66) help maintain a significantly compressive force between jaws (42, 44). With severed tissue layer portions being compressed between jaws (42, 44), bipolar RF energy is applied to the tissue through electrode surfaces (50, 52) by the user depressing activation button (26). Thus, a bipolar RF current flows through the compressed regions of severed tissue layer portions. The bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Alternative Electrosurgical Instrument

In some instances, it may be desirable to provide visual emphasis of the degree of articulation in an articulation section (36). It may also be desirable to indicate to an operator the direction in which articulation section (36) is articulated during operation, the degree to which articulation section (36) is articulated, and/or the manner in which end effector (36) will rotate when knob (34) is rotated. This may be particularly desirable when the operator wishes to rotate end effector (40) via knob (34) while articulation section (36) is in an articulated state. Indications may be provided to the operator through visual markings on handpiece (20), on articulation section (36), and/or on end effector (40). In settings where instrument (10) is being used in a minimally invasive procedure under endoscopic guidance, having visual markings on articulation section (36) and/or on end effector (40) may enable the operator to receive real time visual feedback via an endoscopic viewing monitor, without having to divert their eyes from a display showing the view from the endoscope. Having visual markings on handpiece (20) may enable the operator to confirm that their manipulation of instrument (10) will be made in accordance with the desired effects at end effector (40). Having visual markings on both handpiece (20) and a component that is within the endoscopic field of view (e.g., articulation section (36) and/or on end effector (40)) may enable the operator to quickly visually correlate the orientation of features on handpiece (20) with the orientation of features within the endoscopic field of view.

Various examples of how features of instrument (10) may be configured to provide visual feedback as indicated above will be described in greater detail; while still other examples will be apparent to those of ordinary skill in the art according to the teachings herein. It should be understood that the articulation section examples described below may function substantially similar to articulation section (36) described above. In particular, the articulation section examples described below are operable to selectively laterally deflect an end effector at various angles relative to a longitudinal axis defined by a sheath like sheath (32). It should also be understood that the knob examples described below may function substantially similar to knob (34) described above. In particular, the knob examples described below are operable to selectively rotate a shaft, an articulation section, and/or an end effector about the longitudinal axis defined by a sheath like sheath (32).

A. Exemplary Articulation Section Indicators

Figure 6:
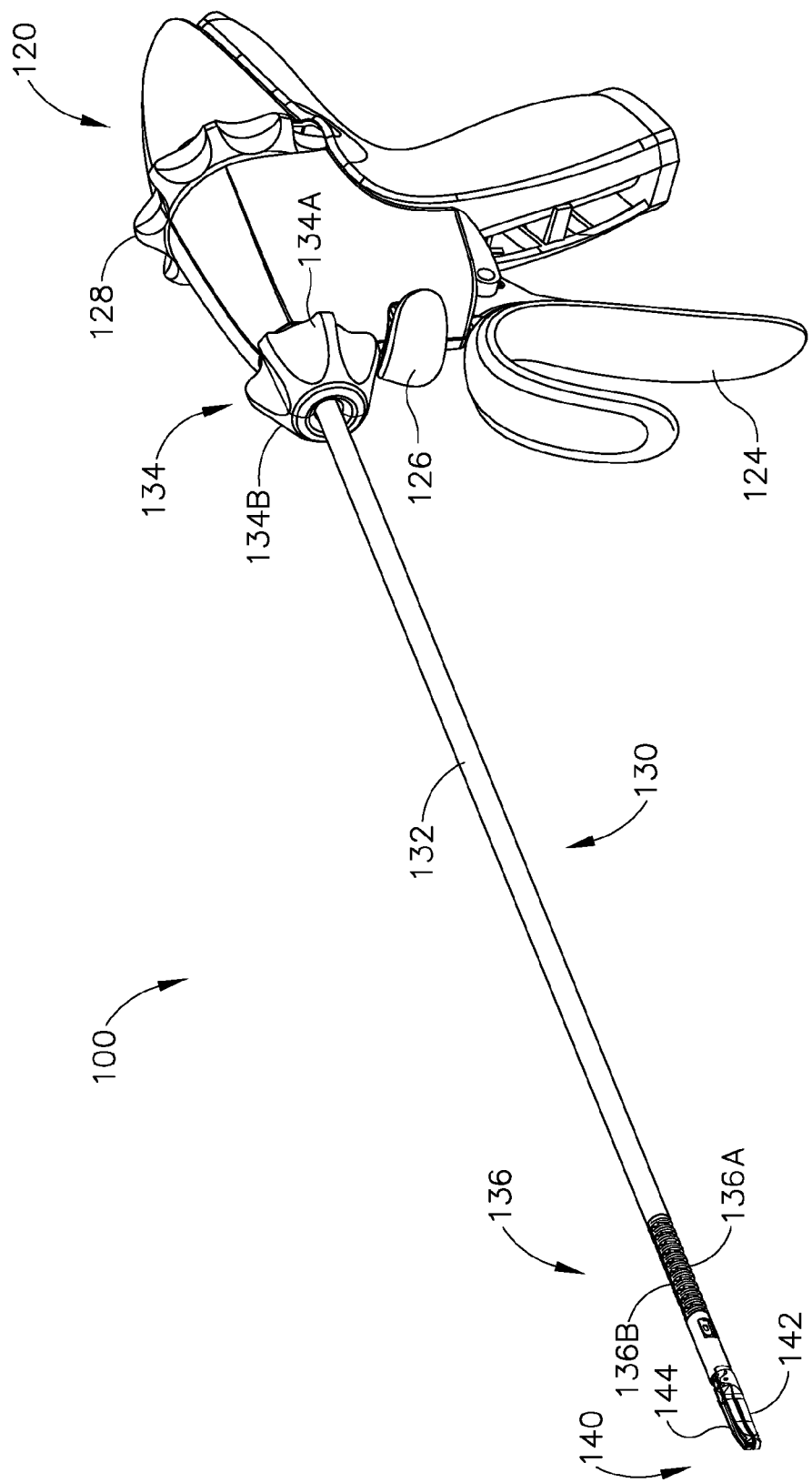
FIG. 6 depicts a perspective view of an exemplary variation of the instrument of FIG. 1.

One merely exemplary variation of an electrosurgical instrument (100) is shown in FIG. 6. Instrument (100) of this example includes a handpiece (120), a shaft (130) extending distally from handpiece (120), and an end effector (140) disposed at a distal end of shaft (130). Shaft (130) of the present example includes a rigid outer sheath (132) and an articulation section (136). End effector (140) of the present example functions substantially similar to end effector (40) described above except for the differences discussed below. In particular, end effector (140) of the present example comprises a first jaw (142) and a second jaw (144). First jaw (142) is substantially fixed relative to a shaft (130); while second jaw (144) pivots relative to shaft (130), toward and away from first jaw (142).

Handpiece (120) of the present example includes a pistol grip (122), a pivoting trigger (124), an activation button (126), an articulation control (128), and a knob (134). Trigger (124) of the present example functions substantially similar to trigger (24) described above. In particular, trigger (124) is pivotable toward and away from pistol grip (122) to selectively actuate end effector (140). Activation button (126) of the present example functions substantially similar to activation button (26) described above. In particular, activation button (126) is operable to selectively activate RF circuitry that is in communication with end effector (140). Articulation control (128) of the present example functions substantially similar to articulation control (28) described above. In particular, articulation control (128) of the present example is operable to selectively control articulation section (136) of shaft (130), to thereby selectively laterally deflect end effector (140) at various angles relative to the longitudinal axis defined by shaft (130). Shaft (130) is rotatable about the longitudinal axis defined by sheath (132), relative to handpiece (120), via knob (134). Such rotation provides rotation of end effector (140) and shaft (130) unitarily. In some other versions, knob (134) is operable to rotate end effector (140) without rotating articulation section (136) or any portion of shaft (130) that is proximal of articulation section (136).

Figure 7:
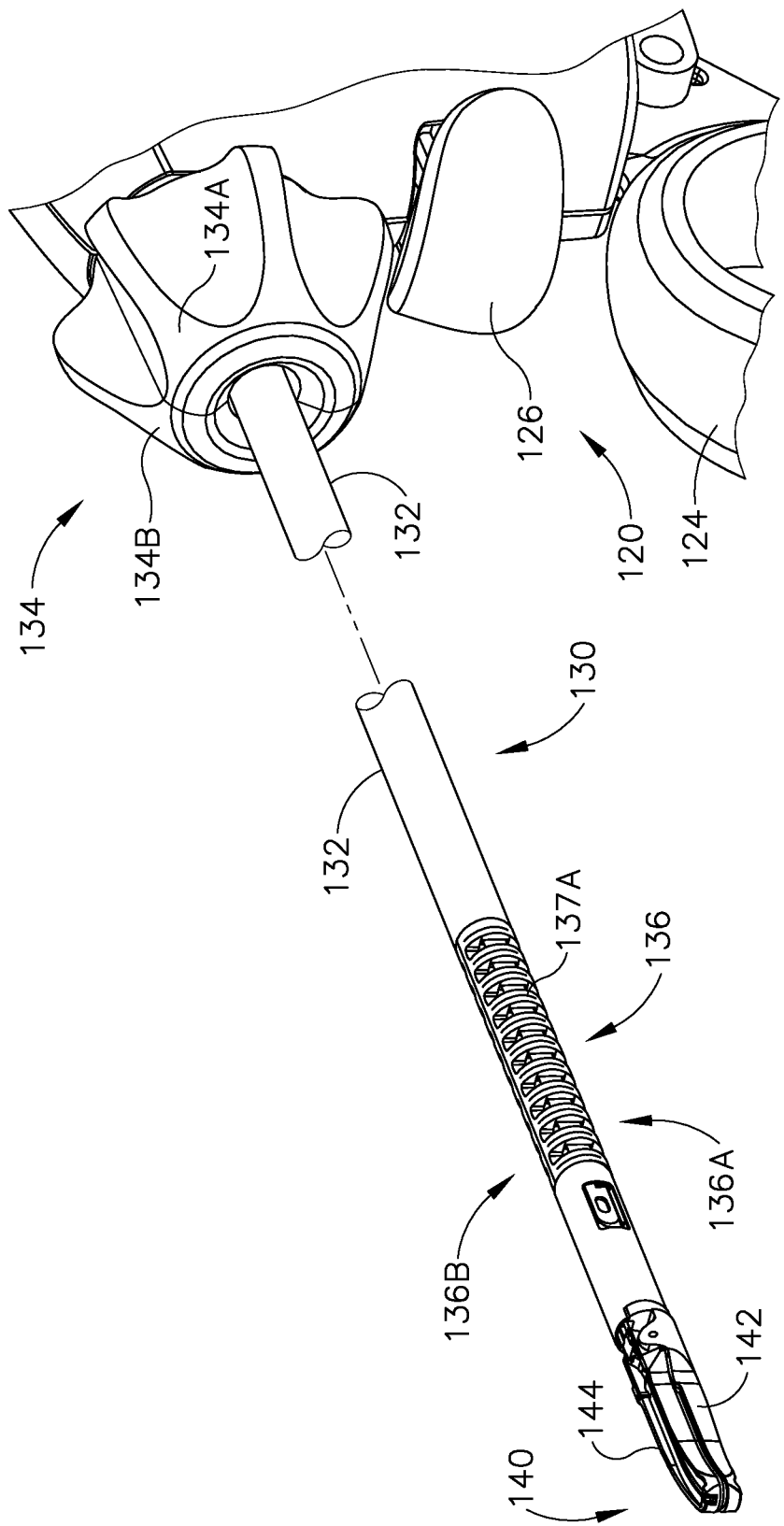
FIG. 7 depicts a detailed perspective view of a shaft assembly and knob of the instrument of FIG. 6.
Figure 8A:
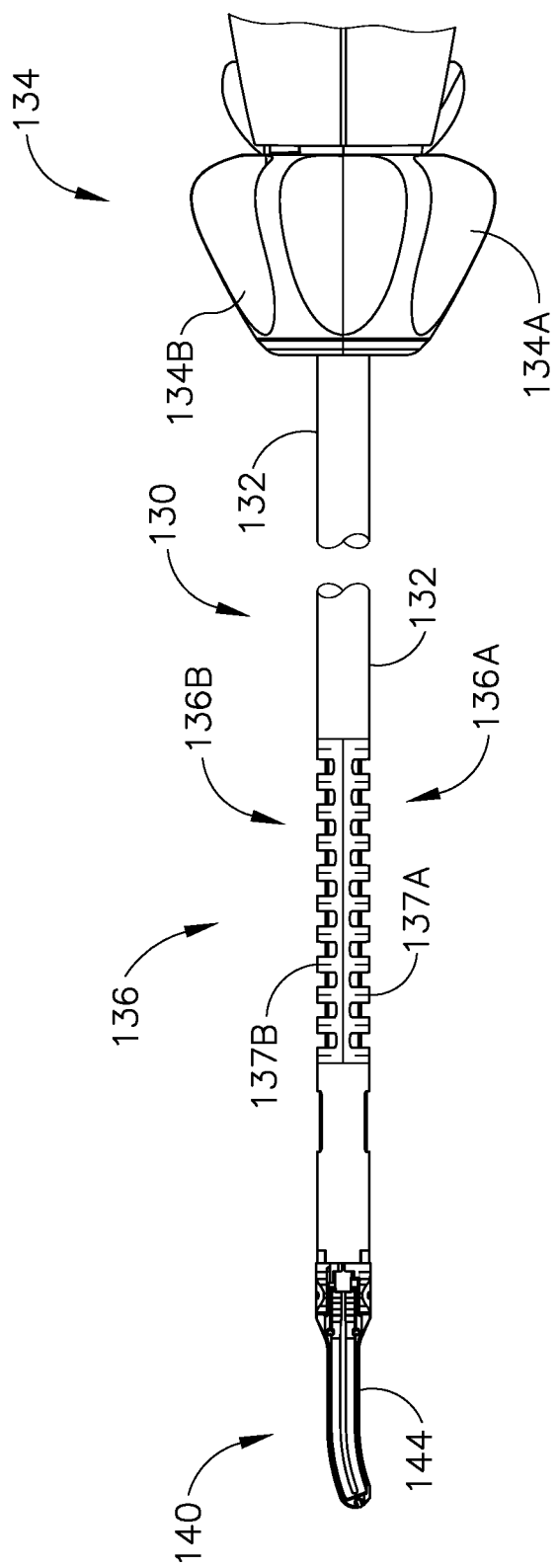
FIG. 8A depicts a top view of the shaft assembly and knob of FIG. 7 in a first position, with an articulation section of the shaft assembly in an unarticulated position.

Articulation section (136) of the present example functions substantially similar to articulation section (36) described above except for the differences discussed below. In particular, articulation section (136) is operable to selectively laterally deflect end effector (140) at various angles relative to a longitudinal axis defined by a sheath (132). As shown in greater detail in FIG. 7, articulation section (136) of the present example presents a first indication section (136A) and a second indication section (136B). First indication section (136A) comprises a first series of indicator markings (137A). Second indication section (136B) comprises a second series of indicator markings (137B). Indicator markings (137A, 137B) of the present example each comprise a series of equally spaced lines disposed on ribs of first indication section (136A) and second indication section (136B). As best seen in FIG. 8A, the series of equally spaced lines of indicator markings (137A, 137B) are oriented such that each line of first series of indicator markings (137A) corresponds to an opposing line of second series of indicator markings (137B) such that first series of indicator markings (137A) and second series of indicator markings (137B) form a symmetric pattern.

Figure 8B:
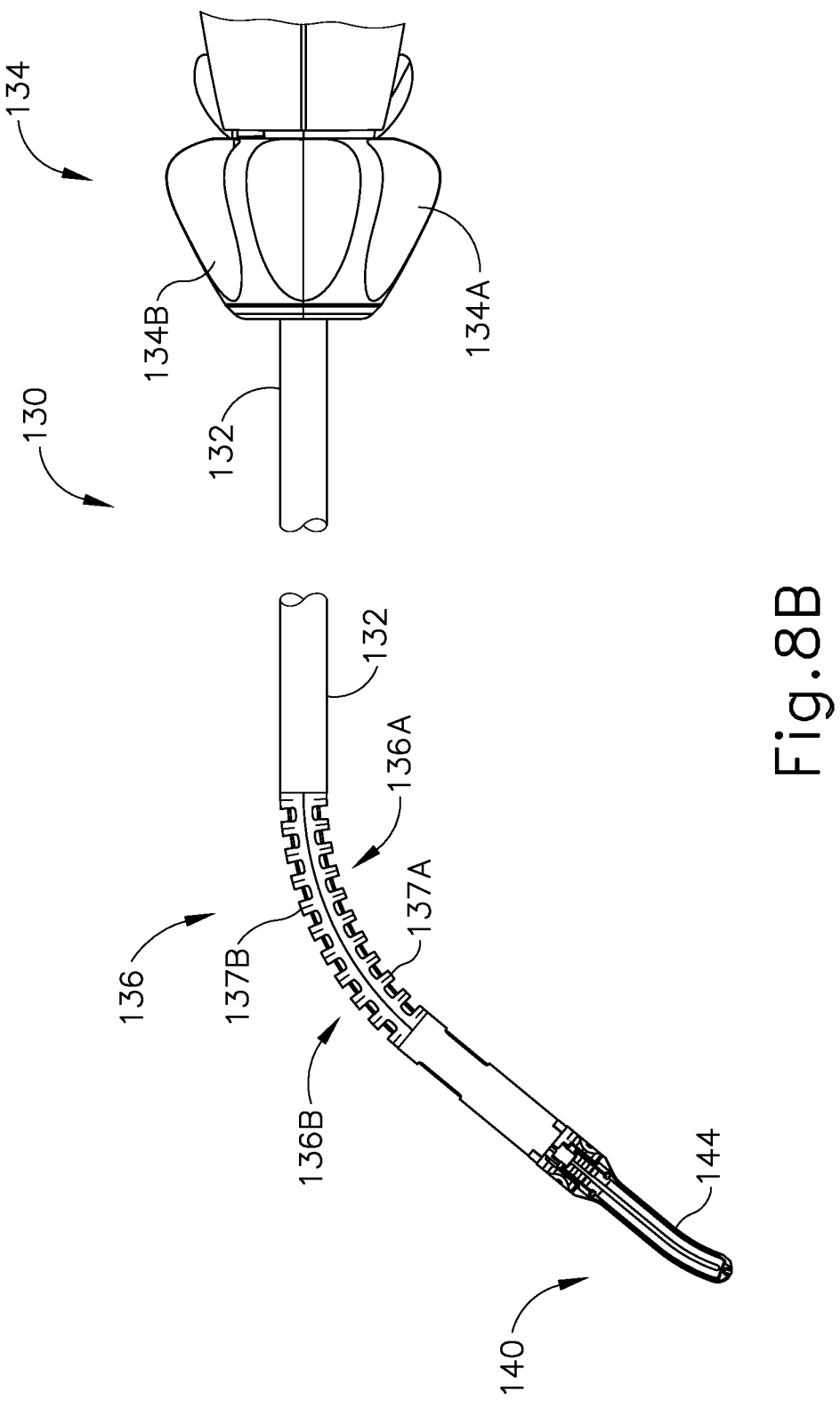
FIG. 8B depicts a top view of the shaft assembly and knob of FIG. 7 in the first position, with the articulation section articulated in a first direction.
Figure 8C:
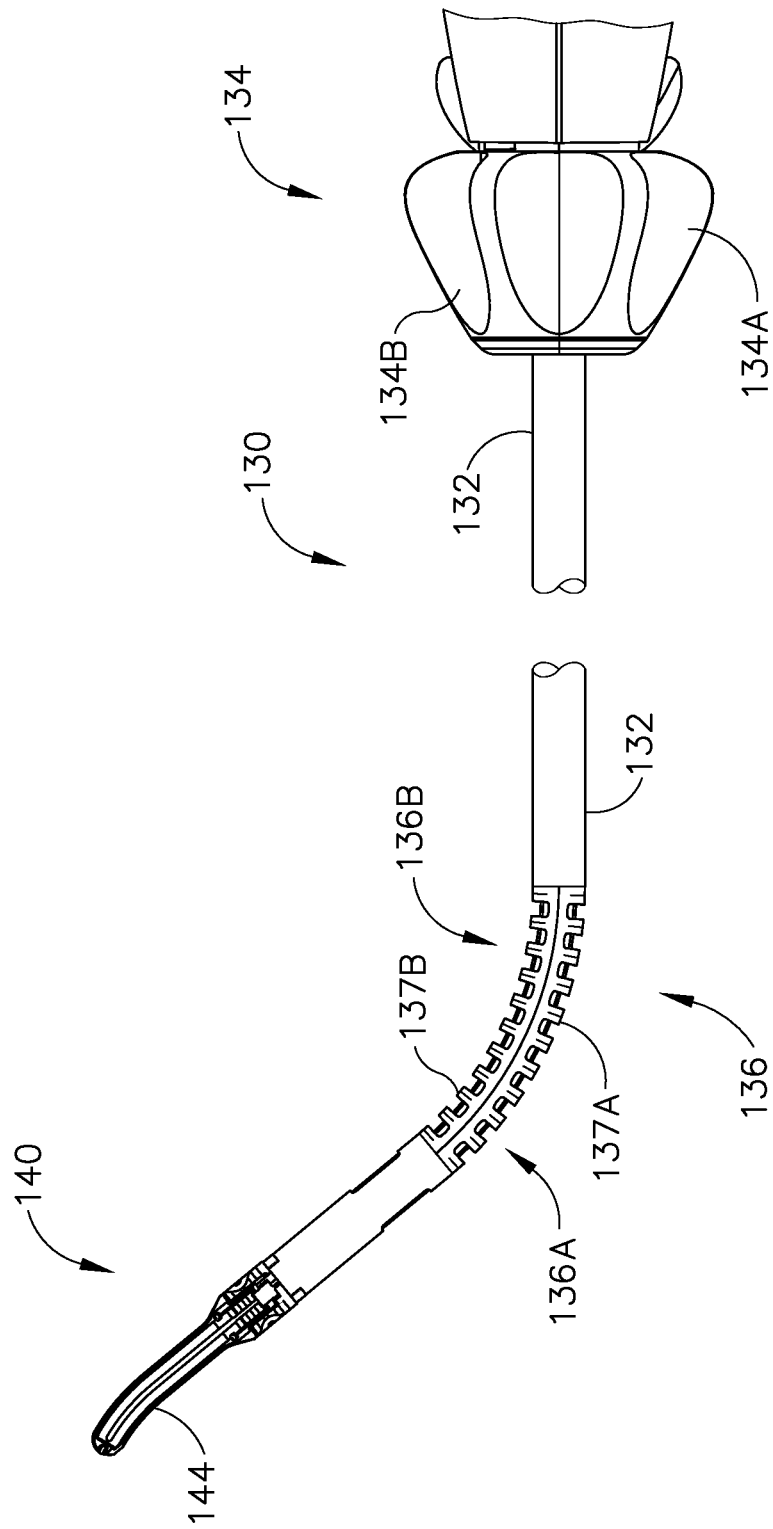
FIG. 8C depicts a top view of the shaft assembly and knob of FIG. 7 in the first position, with the articulation section articulated in a second direction.

When articulation section (136) is in a straight, non-articulated configuration as shown in FIG. 8A, the spacing between markings (137A) is equal to the spacing between markings (137B). Thus, by seeing the consistency between the spacing of markings (137A) and markings (137B) on an endoscopic viewing monitor, an operator will receive visual confirmation that articulation section (136) is in a straight, non-articulated configuration, without having to divert their eyes from the view of the surgical field on the endoscopic viewing monitor. As shown in FIGS. 8B-8C, depending upon the direction in which articulation section (136) is articulated, the spacing between indicator markings (137A, 137B) is opposingly decreased or increased to indicate to an operator the direction in which articulation section (136) is articulated. For instance, as shown in FIG. 8B, articulation section (136) has been articulated toward indication section (136A). Such articulation causes the spacing between the lines of indicator marking (137A) to decrease and the spacing between the lines of indicator markings (137B) to increase. Therefore, upon viewing the spacing of the lines of indicator markings (137A, 137B), an operator could readily confirm that articulation section (136) was articulated toward indication section (136A); and further ascertain the degree of articulation. Alternatively, as shown in FIG. 8C, articulation section (136) has been articulated toward indication section (136B). Such articulation causes the spacing between the lines of indicator marking (137B) to decrease and the spacing between the lines of indicator markings (137A) to increase. Therefore, upon viewing the spacing of the lines of indicator markings (137A, 137B), an operator could readily confirm that articulation section (136) was articulated toward indication section (136B); and further ascertain the degree of articulation.

It should be understood from the foregoing that indicator markings (137A, 137B) may provide ready visual confirmation of the articulated state of articulation section; and that indicator markings (137A, 137B) may further provide visual emphasis of the degree of articulation in articulation section (136). Although indicator markings (137A, 137B) of the present example comprise a series of equally spaced lines, it should be understood that indicator markings (137A, 137B) may take any form as would be apparent to one of ordinary skill in the art according to the teachings herein.

B. Exemplary Articulation Section and Knob Indicators

Figure 9:
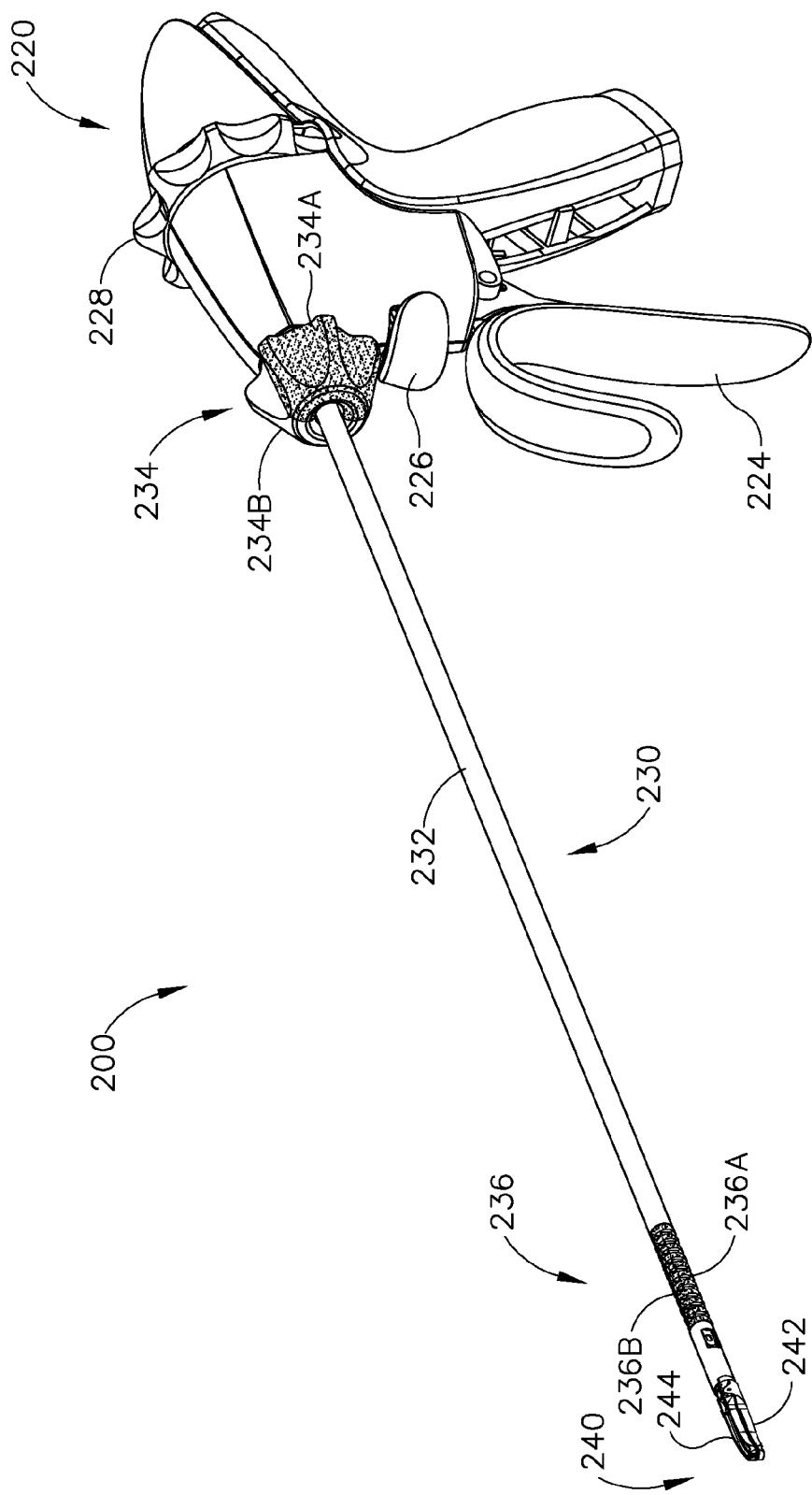
FIG. 9 depicts a perspective view of another exemplary variation of the instrument of FIG. 1.

Another merely exemplary variation of an electrosurgical instrument (200) is shown in FIG. 9. Instrument (200) of this example includes a handpiece (220), a shaft (230) extending distally from handpiece (220), and an end effector (240) disposed at a distal end of shaft (230). Shaft (230) of the present example includes a rigid outer sheath (232) and an articulation section (236). End effector (240) of the present example functions substantially similar to end effector (40) described above. In particular, end effector (240) of the present example comprises a first jaw (242) and a second jaw (244). First jaw (242) is substantially fixed relative to a shaft (230); while second jaw (244) pivots relative to shaft (230), toward and away from first jaw (242).

Handpiece (220) of the present example includes a pistol grip (222), a pivoting trigger (224), an activation button (226), an articulation control (228), and a knob (234). Trigger (224) of the present example functions substantially similar to trigger (24) described above. In particular, trigger (224) is pivotable toward and away from pistol grip (222) to selectively actuate end effector (240). Activation button (226) of the present example functions substantially similar to activation button (26) described above. In particular, activation button (226) is operable to selectively activate RF circuitry that is in communication with end effector (240). Articulation control (228) of the present example functions substantially similar to articulation control (28) described above. In particular, articulation control (228) of the present example is operable to selectively control articulation section (236) of shaft (230), to thereby selectively laterally deflect end effector (240) at various angles relative to the longitudinal axis defined by shaft (230). Shaft (230) is rotatable about the longitudinal axis defined by sheath (232), relative to handpiece (220), via knob (234). Such rotation provides rotation of end effector (240) and shaft (230) unitarily. In some other versions, knob (234) is operable to rotate end effector (240) without rotating articulation section (236) or any portion of shaft (230) that is proximal of articulation section (236).

Figure 10:
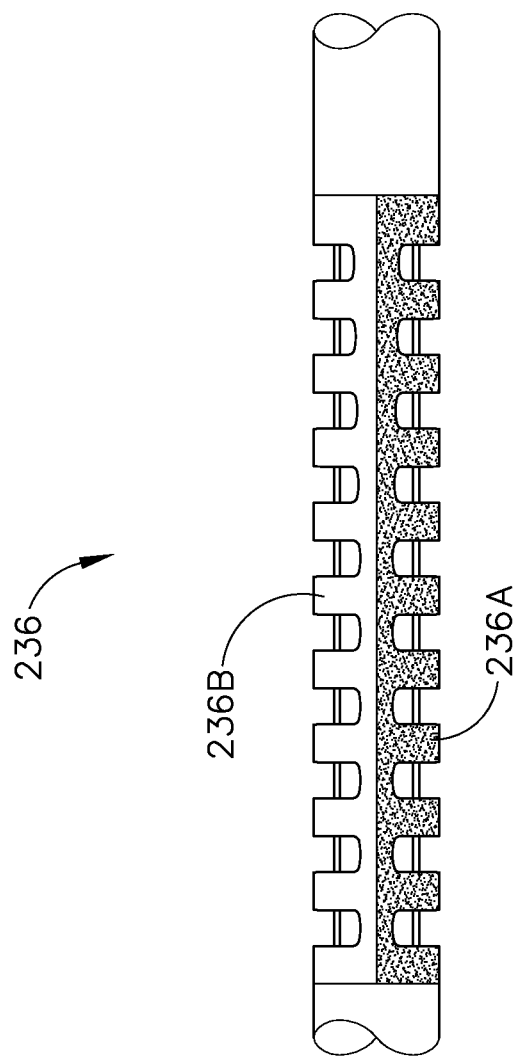
FIG. 10 depicts a detailed top view of an articulation section of the instrument of FIG. 9.

Articulation section (236) of the present example functions substantially similar to articulation section (36) described above except for the differences discussed below. In particular, articulation section (236) is operable to selectively laterally deflect end effector (240) at various angles relative to a longitudinal axis defined by a sheath (232). As shown in greater detail in FIG. 10, articulation section (236) of the present example presents a first indication section (236A) and a second indication section (236B). Indication sections (236A, 236B) of articulation section (236) comprise different colors such that first indication section (236A) comprises a first color and second indication section (236B) comprises a second color. While only two indication sections (236A, 236B) are used in the present example, it should be understood that any other suitable number of indication sections may be used. By way of example only, articulation section (236) may have three indication sections that each extend through a range of approximately 120° about the perimeter of articulation section (236). As another merely illustrative example, articulation section (236) may have four indication sections that each extend through a range of approximately 90° about the perimeter of articulation section (236). Other suitable ways in which articulation section (236) may be divided into sectors by indication sections will be apparent to those of ordinary skill in the art in view of the teachings herein.

Figure 11:
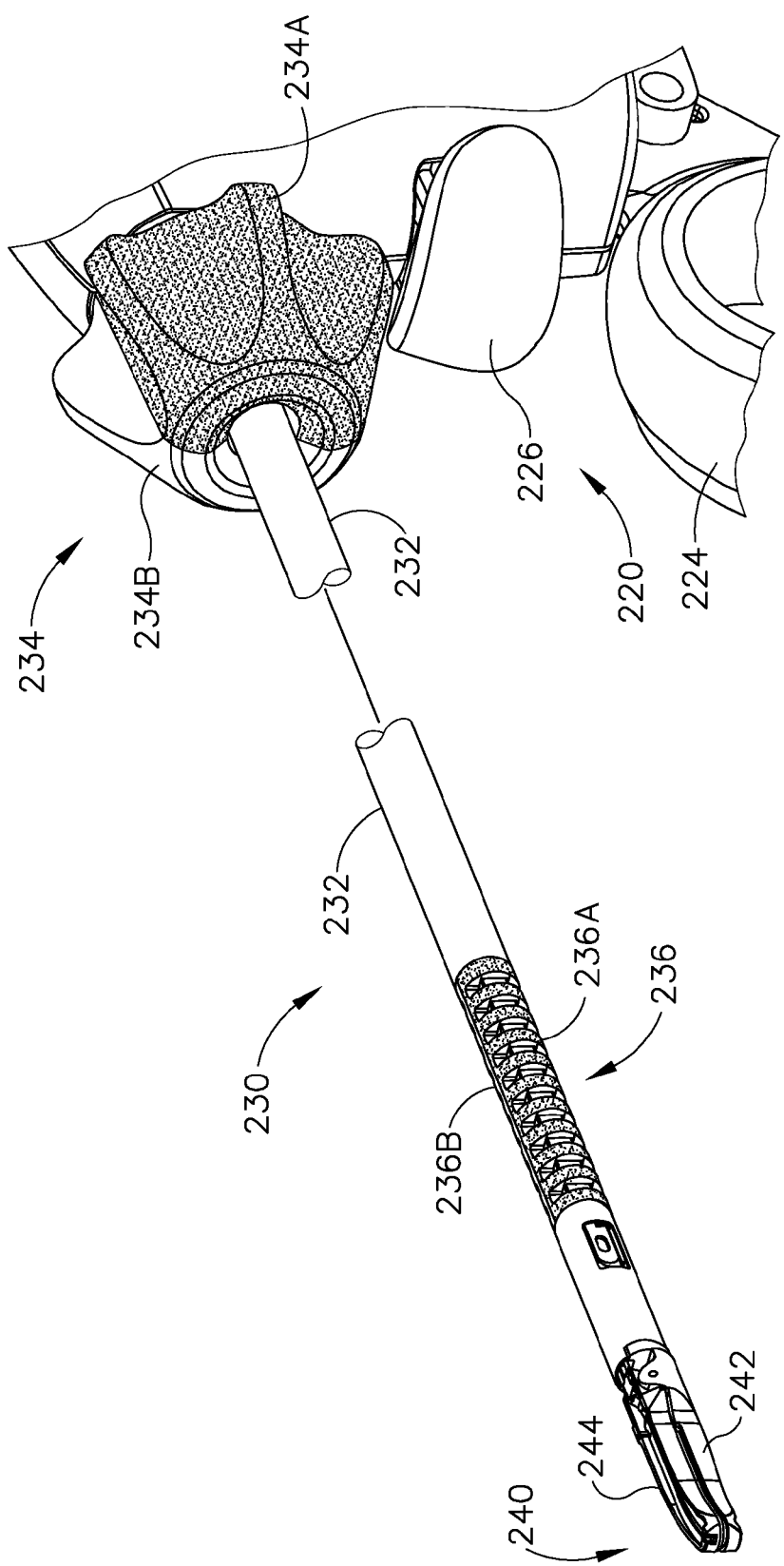
FIG. 11 depicts a detailed perspective view of a shaft assembly and knob of the instrument of FIG. 9.

As best seen in FIG. 11, knob (234) of the present example presents a first indication section (234A) and a second indication section (234B). Indication sections (234A, 234B) of knob (234) comprise different colors such that first indication section (234A) comprises a first color and second indication section (234B) comprises a second color. In the present example, the particular color of indication section (234A) of knob (234) matches the particular color of indication section (236A) of articulation section (236); and the particular color of indication section (234B) of knob (234) matches the particular color of indication section (236B) of articulation section (236). Also in the present example, indication section (234A) of knob (234) is oriented such that indication section (234A) of knob (234) aligns with indication sections (236A) of articulation section (236); and indication section (234B) of knob (234) is oriented such that indication section (234B) of knob (234) aligns with indication sections (236B) of articulation section (236). Indication section (234A) thus fully complements and corresponds with indication section (236A); while indication section (234B) fully complements and corresponds with indication section (236B).

While only two indication sections (234A, 234B) are used in the present example, it should be understood that any other suitable number of indication sections may be used. By way of example only, knob (234) may have three indication sections that each extend through a range of approximately 120° about the perimeter of knob (234). As another merely illustrative example, knob (234) may have four indication sections that each extend through a range of approximately 90° about the perimeter of knob (234). Other suitable ways in which knob (234) may be divided into sectors by indication sections will be apparent to those of ordinary skill in the art in view of the teachings herein. It should be understood that variations in the number/arrangement of indication sections in knob (234) may be complemented by a corresponding number/arrangement of indication sections in articulation section (236).

Figure 12A:
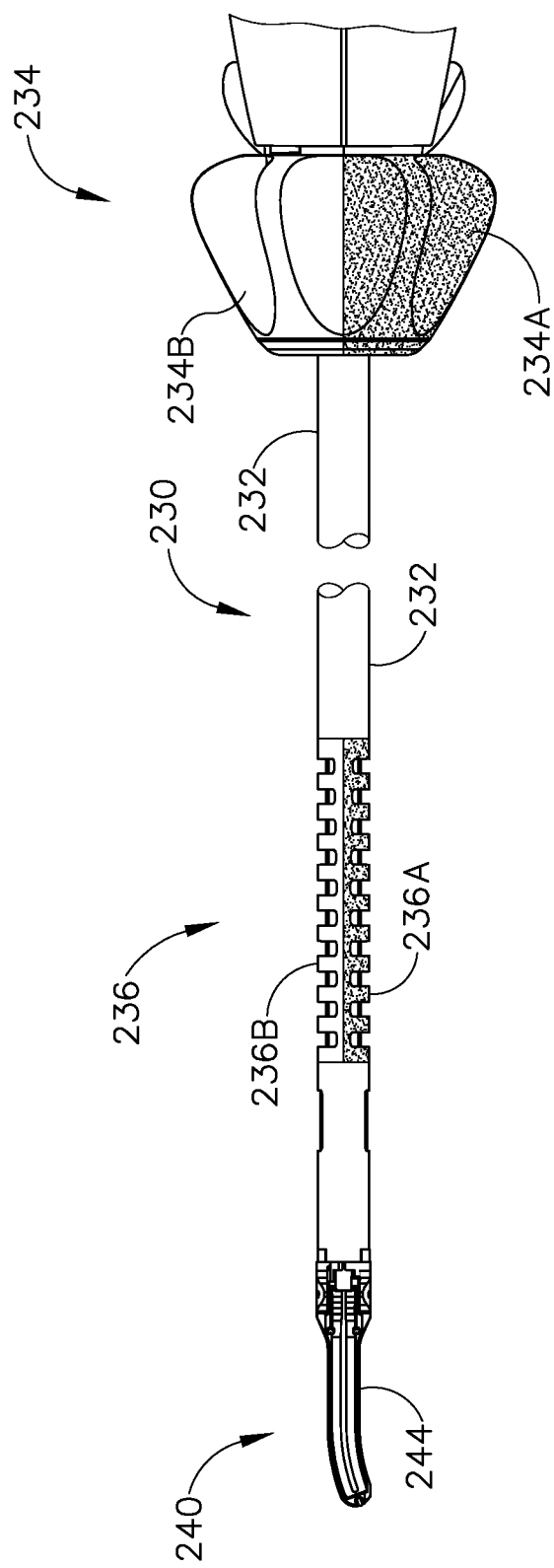
FIG. 12A depicts a top view of the shaft assembly and knob of FIG. 11 in a first rotational position.
Figure 12B:
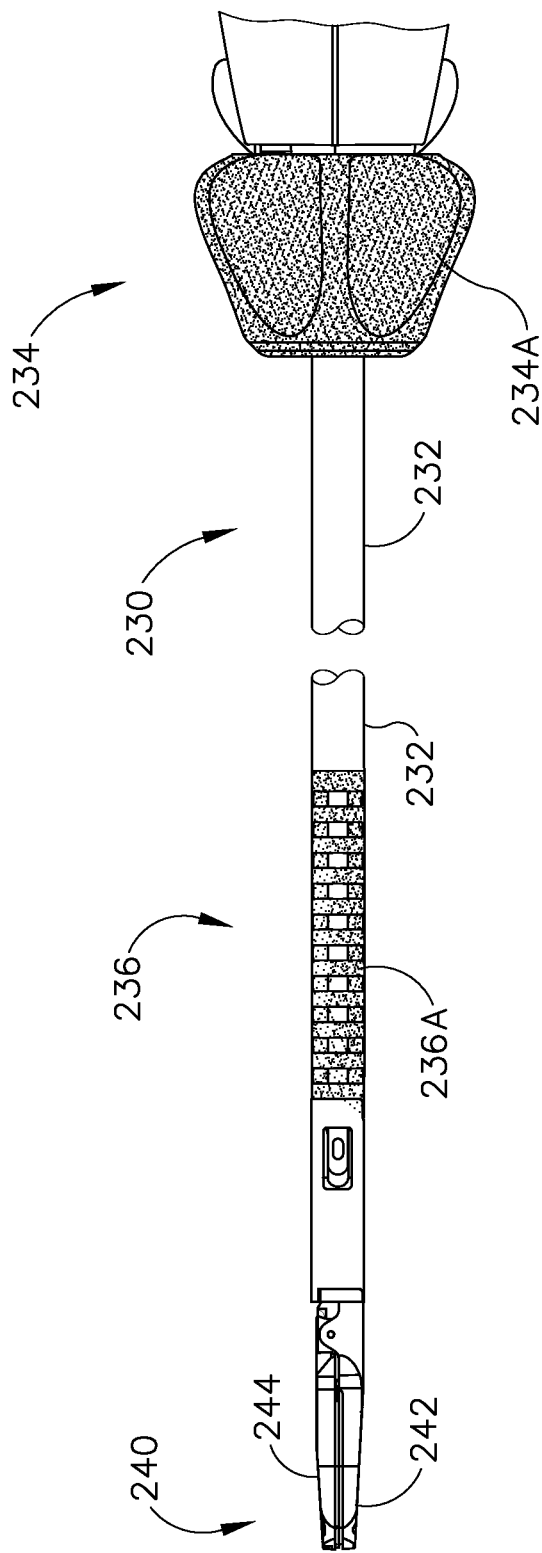
FIG. 12B depicts a top view of the shaft assembly and knob of FIG. 11 rotated to a second rotational position, which is 90° from the first rotational position, with the articulation section of FIG. 10 in an unarticulated position.
Figure 12C:
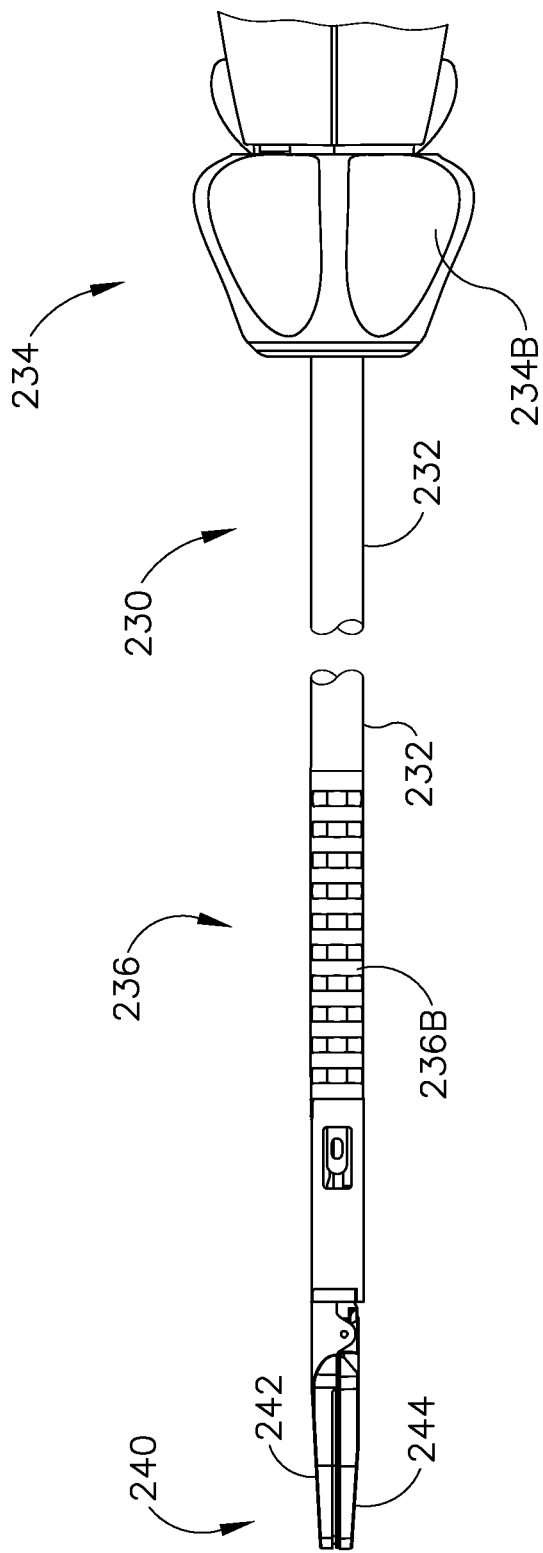
FIG. 12C depicts a top view of the shaft assembly and knob of FIG. 11 rotated to a third rotational position, which is 270° from the first rotational position, with the articulation section of FIG. 10 in an unarticulated position.

As shown in FIGS. 12A-12C, in versions of instrument (200) in which knob (234) is operable to rotate end effector (240) and shaft (230) unitarily, indication sections (234A, 234B) of knob (234) will remain aligned with indication sections (236A, 236B) of articulation section (236) as knob (234), shaft (230), and end effector (240) are rotated unitarily by knob (234). It should be understood that, during operation, end effector (240) and articulation section (236) may be viewable on an external monitor (not shown) via an endoscopic camera (not shown). It should also be understood that, during operation, knob (234) would be viewable outside a patient. Thus, if the operator wishes to rotate end effector (240) while end effector (240) is positioned within the patient, the operator will be able to readily understand the angular orientation of end effector (240) in relation to knob (234) by visually correlating viewable indication section(s) (236A, 236B) with indication section(s) (234A, 234B). This may further enable the operator to readily discern the direction in which articulation section (236) will rotate when the operator rotates knob (234).

Although indication sections (234A, 234B, 236A, 236B) of the present example particular colors, it should be understood that indication sections (234A, 234B, 236A, 236B) may take any form and would be apparent to one of ordinary skill in the art according to the teachings herein. By way of example only, indication sections (234A, 234B, 236A, 236B) may include visually distinguishable patterns and/or other readily distinguishable features. It should be understood that any of the indication sections and/or indication markings discussed above could be combined with one another. For instance, the series equally spaced lines of indicator markings (137A, 137B) discussed above could be combined with the particular colors of indication sections (234A, 234B, 236A, 236B). Other suitable features that may be used to provide ready visual confirmation of states of operation of an instrument will be apparent to those of ordinary skill in the art in view of the teachings herein.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with mechanical and Electrical Feedback," published May 10, 2012, now U.S. Pat. No. 9,161,803, Issued on Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S.

Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010 (now U.S. Pat. No. 8,408,439); and U.S. Pub. No. 2012/0239012, entitled "Motor-Driven Surgical Cutting Instrument with Electric Actuator Directional Control Assembly," published Sep. 20, 2012 (now U.S. Pat. No. 8,453,914). Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011 know U.S. Pat. No. 8,461,744), the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011 (now U.S. Pat. No. 8,939,974), the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body;
   (b) an elongate shaft, wherein the elongate shaft extends distally from the body, wherein the elongate shaft defines a longitudinal axis, wherein the elongate shaft comprises a proximal portion, a distal portion, and an articulation section, wherein the articulation section is located at the distal portion, wherein the articulation section comprises:
      i. a plurality of ribs having a first side and an opposite second side;
      ii. a first indication section corresponding to a first direction of articulation, wherein the first indication section includes a first visually distinctive feature, wherein the first visually distinctive feature includes a first series of lines disposed on the first side of the plurality of ribs, and
      iii. a second indication section corresponding to a second direction of articulation, wherein the second indication section includes a second visually distinctive feature, wherein the second visually distinctive feature includes a second series of lines disposed on the second opposite side of the plurality of ribs; and
   (c) an end effector positioned distal to the articulation section, wherein the first indication section and the second indication section are located at the distal portion of the elongate shaft proximal to the end effector, wherein the articulation section is configured to selectively laterally deflect the end effector relative to the longitudinal axis defined by the elongate shaft in the first direction of articulation and in the second direction of articulation;
   wherein the first visually distinctive feature and the second visually distinctive feature are configured to provide visual indication of whether the articulation section is deflected in the first direction of articulation or the second direction of articulation.

2. The apparatus of claim 1, wherein the first series of lines are equally spaced, wherein the second series of lines are equally spaced.

3. The apparatus of claim 2, wherein each line of the first series of equally spaced lines are opposed to the second series of equally spaced lines such that the first series of equally spaced lines and the second series of equally spaced lines forms a symmetric pattern.

4. The apparatus of claim 1, wherein the first visually distinctive feature comprises a first color, wherein the second visually distinctive feature comprises a second color.

5. The apparatus of claim 1, wherein the elongate shaft, the articulation section, and the end effector are configured to rotate unitarily.

6. The apparatus of claim 1, wherein the body comprises a rotation knob, and wherein the rotation knob is configured to cause rotation of the articulation section.

7. The apparatus of claim 6, wherein the rotation knob comprises a third indication section and a fourth indication section, wherein the third indication section is visually distinguishable from the fourth indication section.

8. The apparatus of claim 7, wherein the first indication section of the articulation section is angularly aligned with the third indication section of the rotation knob, wherein the second indication section of the articulation section is angularly aligned with the fourth indication section of the rotation knob.

9. The apparatus of claim 8, wherein the third indication section of the rotation knob includes a third visually distinctive feature, wherein the fourth indication section of the rotation knob includes a fourth visually distinctive feature.

10. The apparatus of claim 9, wherein the third visually distinctive feature is substantially similar to the first visually distinctive feature; wherein the fourth visually distinctive feature is substantially similar to the second visually distinctive feature.

11. The apparatus of claim 10, wherein the first visually distinctive feature and the second visually distinctive feature have a first color, wherein the second visually distinctive feature and the fourth visually distinctive feature have a second color.

12. The apparatus of claim 1, wherein the body comprises an articulation control, wherein the articulation control is configured to selectively control articulation of the articulation section.

13. The apparatus of claim 1, wherein the end effector comprises:
   (i) a first jaw, and
   (ii) a second jaw, wherein the first jaw is selectively pivotable toward and away from the second jaw.

14. The apparatus of claim 13, wherein the end effector comprises at least one electrode operable to apply radiofrequency energy to tissue.

15. An apparatus for operating on tissue; the apparatus comprising:
   (a) a body;
   (b) an elongate shaft comprising a proximal end, a distal end, and an articulation section, wherein the elongate shaft extends distally from the body, wherein the elongate shaft defines a longitudinal axis, wherein the articulation section comprises a first indication section disposed on a first side of a plurality of ribs distal from the body, wherein the first indication section includes a first visually distinctive feature;
   (c) an end effector, wherein the end effector is disposed at the distal end of the elongate shaft, wherein the articulation section is configured to selectively laterally deflect the end effector relative to the longitudinal axis defined by the elongate shaft in a first direction of articulation and in a second direction of articulation; and
   wherein the first visually distinctive feature is configured to provide visual indication of whether the articulation section is deflected in the first direction of articulation or the second direction of articulation;
   wherein the first visually distinctive feature includes a series of equally spaced lines, wherein each line in the series of equally spaced lines is disposed on a corresponding rib in the plurality of ribs;
   wherein the articulation section further comprises a second indication section disposed on a second side of the plurality of ribs;
   wherein the first indication section is visually distinct from the second indication section, wherein the visual distinction between the first and second indication sections is directly visually observable.

* * * * *